United States Patent
Pan et al.

(10) Patent No.: US 7,569,530 B1
(45) Date of Patent: *Aug. 4, 2009

(54) ANTIMICROBIAL COMPOSITIONS, PRODUCTS AND METHODS EMPLOYING SAME

(75) Inventors: Robert Ya-Lin Pan, Cincinnati, OH (US); Rosa Laura Moese, West Chester, OH (US); Abel Saud, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/600,180

(22) Filed: Jun. 20, 2003

(51) Int. Cl.
*A61K 7/00* (2006.01)
(52) U.S. Cl. ............... 510/130; 510/426; 510/434; 510/477; 510/492
(58) Field of Classification Search ......... 510/130, 510/156, 438, 424, 426
See application file for complete search history.

(56) References Cited

U.S. PATENT DOCUMENTS

| | | | |
|---|---|---|---|
| 3,141,821 A | 7/1964 | Compeau | |
| 3,933,672 A | 1/1976 | Bartolotta et al. | |
| 4,136,045 A | 1/1979 | Gault et al. | |
| 4,376,787 A | 3/1983 | Lentsch et al. | |
| 4,828,912 A | 5/1989 | Hossain et al. | |
| 4,863,629 A | 9/1989 | Osberghaus et al. | |
| 4,865,855 A | 9/1989 | Hansen et al. | |
| 5,006,529 A | 4/1991 | Resch | |
| 5,057,246 A | 10/1991 | Bertho et al. | |
| 5,143,720 A | 9/1992 | Lopes | |
| 5,280,042 A | 1/1994 | Lopes | |
| 5,322,643 A | 6/1994 | Schwartz et al. | |
| 5,324,443 A | 6/1994 | Arif et al. | |
| 5,460,833 A | 10/1995 | Andrews et al. | |
| 5,490,992 A | 2/1996 | Andrews et al. | |
| 5,523,324 A | 6/1996 | Subramanyam et al. | |
| 5,554,597 A | 9/1996 | Yu | |
| 5,567,359 A | 10/1996 | Cassidy et al. | |
| 5,591,442 A | 1/1997 | Diehl et al. | |
| 5,610,189 A | 3/1997 | Whiteley | |
| 5,653,970 A | 8/1997 | Vermeer | |
| 5,736,574 A | 4/1998 | Burnier et al. | |
| 5,798,329 A * | 8/1998 | Taylor et al. ............... 510/384 |
| 5,942,478 A | 8/1999 | Lopes | |
| 5,965,513 A | 10/1999 | Allan et al. | |
| 5,968,539 A | 10/1999 | Beerse et al. | |
| 5,977,041 A | 11/1999 | Honda | |
| 6,020,375 A | 2/2000 | Nishihata et al. | |
| 6,066,674 A | 5/2000 | Hioki et al. | |
| 6,071,961 A | 6/2000 | Wider | |
| 6,083,890 A | 7/2000 | Miskiel et al. | |
| 6,110,445 A | 8/2000 | Gaffar et al. | |
| 6,183,757 B1 | 2/2001 | Beerse et al. | |
| 6,190,674 B1 | 2/2001 | Beerse et al. | |
| 6,190,675 B1 * | 2/2001 | Beerse et al. ............... 424/401 |
| 6,210,695 B1 | 4/2001 | Beerse et al. | |
| 6,217,887 B1 | 4/2001 | Beerse et al. | |
| 6,231,843 B1 | 5/2001 | Hoelzel et al. | |
| 6,262,038 B1 | 7/2001 | Pierce et al. | |
| 6,287,577 B1 | 9/2001 | Beerse et al. | |
| 6,294,186 B1 | 9/2001 | Beerse et al. | |
| 6,416,768 B1 | 7/2002 | Ravaux et al. | |
| 6,417,146 B1 | 7/2002 | Miyajima et al. | |
| 6,517,849 B1 | 2/2003 | Seger et al. | |
| 6,894,012 B2 | 5/2005 | Sebillotte-Arnaud et al. | |
| 2002/0098159 A1 | 7/2002 | Wei et al. | |
| 2002/0182238 A1 | 12/2002 | Creton | |
| 2002/0192407 A1 | 12/2002 | Hendrix et al. | |
| 2003/0152644 A1 | 8/2003 | Modak et al. | |
| 2004/0234457 A1 | 11/2004 | Rennie et al. | |
| 2006/0078583 A1 | 4/2006 | Rennie et al. | |

FOREIGN PATENT DOCUMENTS

| | | |
|---|---|---|
| DE | 32 29 097 A1 | 2/1984 |
| JP | 10-158691 | 6/1998 |
| JP | 11-323378 | 11/1999 |
| WO | WO 91/09924 | 7/1991 |
| WO | WO 91/09924 A1 | 7/1991 |
| WO | WO 91/09931 | 7/1991 |
| WO | WO 96/09761 | 4/1996 |
| WO | WO 98/37866 A1 | 9/1998 |

(Continued)

OTHER PUBLICATIONS

Dychdala, G.R. and Lopes, John A., "Surface-Active Agents: Acid-Anionic Compounds," *Disinfectants And Antiseptics. A. By Chemical Type*, Chapter 14, pp. 256-262.

(Continued)

*Primary Examiner*—Necholus Ogden, Jr.
(74) *Attorney, Agent, or Firm*—Brinks Hofer Gilson & Lione

(57) ABSTRACT

Antimicrobial compositions that provide enhanced immediate and residual anti-viral and antibacterial efficacy against rhinovirus, rotavirus, coronovirus, respiratory syncytial virus, Gram-positive bacteria, Gram-negative bacteria and combinations thereof. More specifically, antimicrobial compositions comprising an organic acid or organic acid mixture and a short-chain anionic surfactant having at least one of a large head group; a branched alkyl chain and an unsaturated alkyl chain. Further, products incorporating the antimicrobial compositions of the present invention and methods of using the antimicrobial compositions and products are disclosed herein.

23 Claims, No Drawings

FOREIGN PATENT DOCUMENTS

| | | |
|---|---|---|
| WO | WO 98/55080 A2 | 12/1998 |
| WO | WO 00/61106 A1 | 10/2000 |
| WO | WO 01/28339 A2 | 4/2001 |
| WO | WO 01/28340 A2 | 4/2001 |
| WO | WO 01/28552 A2 | 4/2001 |
| WO | WO 01/51599 A1 | 7/2001 |
| WO | WO 02/080668 A2 | 10/2002 |
| WO | WO 2005/074990 A2 | 8/2005 |

OTHER PUBLICATIONS

Blease et al., "Surfactant Antifoams", *Defoaming, Theory and Industrial Applications*, Marcel Dekker, New York, 1973, pp. 299-323.

U.S. Appl. No. 10/177,445, filed Jun. 21, 2002, Saud et al.

U.S. Appl. No. 10/263,211, filed Oct. 2, 2002, Pan et al.

\* cited by examiner

ANTIMICROBIAL COMPOSITIONS, PRODUCTS AND METHODS EMPLOYING SAME

CROSS REFERENCE TO RELATED APPLICATIONS

This application claims priority, in part, to application Ser. No. 10/177,445, filed on 21 Jun. 2002 and application Ser. No. 10/263,211, filed on 2 Oct. 2002, both of which are still pending before the United States Patent and Trademark Office.

FIELD OF THE INVENTION

The present invention relates to antimicrobial compositions, products incorporating said antimicrobial compositions and methods of using the present antimicrobial compositions and products. More specifically, the present invention relates to antimicrobial compositions comprising an organic acid or organic acid mixture, a specific, short-chain anionic surfactant having at least one of the following: a large, hydrophilic head group; an unsaturated structure; and/or a branched structure.

BACKGROUND OF THE INVENTION

Human and mammalian health is certainly impacted by the spread of microbial entities at home, school, work and in the environment generally. Indeed, viruses and bacteria continue to cause a variety of sicknesses and ailments, prompting high absenteeism in schools and places of employment. In the wake of widespread food poisoning and the like, the public has become even further concerned with sanitization, both of person and property. Consequently, those of skill in the art have focused their research endeavors on the identification and deployment of suitable antimicrobial compositions, and specifically those that provide immediate and residual kill of microbes, with or without the use of water.

A comprehension of the vast benefits achieved via practice of the present invention requires an understanding of the various microbes against which the present compositions are effective. Bacteria found on human skin may be divided into two groups, namely, resident and transient bacteria. Resident bacteria are Gram-positive bacteria that establish as permanent microcolonies on the surface and outermost layers of the skin. Such bacteria play a fundamental role in preventing the colonization of other, more harmful bacteria and fungi. Transient bacteria are bacteria that are not part of the normal resident of the flora of the skin. Rather, transient bacteria are deposited when airborne contaminated material lands on the skin or when contaminated material is brought into physical contact with such bacteria. Transient bacteria are typically divided into two subgroups: Gram-positive and Gram-negative. Gram-positive bacteria include pathogens such as *Staphylococcus aureus, Streptococcus pyogenes* and *Clostridium botulinum*. Gram-negative bacteria include pathogens such as *Salmonella, Escherichia coli, Klebsiella, Haemophilus, Pseudomonas aeuginosa, Proteus* and *Shigella dysenteriae*. Gram-negative bacteria are generally distinguished from Gram-positive bacteria via the existence of an additional protective cell membrane in the former, which often results in Gram-negative bacteria being less susceptible to conventional, topical antibacterial actives.

There exist several contemporary compositions and methods for reducing and/or eliminating the formation of bacteria and/or viruses. For example, it is well known that the washing of hard surfaces, food (e.g. fruit or vegetables) and skin, especially the hands, with antimicrobial or non-medicated soap, is effective against viruses and bacteria. Actually, removal of the viruses and bacteria is due to the surfactancy of the soap and the mechanical action of the wash procedure, rather than the function of an antimicrobial agent. Thus, it is recommended that people wash frequently to reduce the spread of viruses and bacteria. However, many conventional products and methods of sanitization, including washing, fail to address the dilemma of sanitization "on the go", that is to say, when a consumer is removed from the benefit of running water. Those skilled in the art have attempted to resolve this dilemma via the incorporation of antimicrobial agents into disinfecting lotions, cleansing wipes and the like. Such articles reduce the need for water during or following the application of the subject composition.

Other conventional antimicrobial cleansing products include deodorant soaps, hard surface cleaners, and surgical disinfectants. These traditional, rinse-off antimicrobial products have been formulated to provide bacteria removal during washing. A few such products, including antimicrobial soaps, have also been shown to provide a residual effectiveness against Gram-positive bacteria, but provide limited residual effectiveness against Gram-negative bacteria. By "residual effectiveness", it is meant that the subject antimicrobial controls microbial growth on a substrate by either preventing growth of microbes or engaging in continuous kill of microbes for some period of time following the washing and/or rinsing process. To address the dilemma of limited residual efficacy against Gram-negative bacteria, those skilled in the art have sought to incorporate high levels of alcohol and/or harsh surfactants into contemporary antimicrobial products, which have been shown to cause dryness and irritation to skin tissues.

Thus, there remains a substantial need to identify and deploy antimicrobial compositions that may be used by consumers "on the go"; provide immediate and residual kill of microbes with or without washing; and prevent dryness and irritation to skin following application. Despite providing a quasi solution to the dilemma of water availability, those skilled in the art have yet to identify antimicrobial compositions that address the problems associated with dryness and irritation to skin. In fact, attempts to resolve this dilemma have generally resulted in the adoption of aqueous-based antimicrobial formulas incorporating high levels of zwitterionic surfactants that are too weak to provide significant immediate or residual benefits. Others have attempted to address the dilemma of dryness or irritation to skin by incorporating cationic surfactants into antimicrobial compositions, which have been associated with adverse impacts on the environment and human health. Yet others still have attempted to resolve this dilemma via the incorporation of long-chain anionic surfactants into antimicrobial compositions, which are intended to prevent skin tissue penetration. Nevertheless, such surfactants are often associated with poor phase stability in product, incompatibility with commercial antimicrobial agents, and low residual kill performance. Indeed, the identification of a balance between the factors of antimicrobial performance, skin mildness and water availability continues to be a key concern to those of skill in the antimicrobial art.

SUMMARY OF THE INVENTION

The present invention addresses and resolves all of the problems associated with the employment of conventional antimicrobial compositions and/or products. Indeed, it has been surprisingly discovered that a composition incorporating an organic acid or organic acid mixture, a specific short-chain anionic surfactant having at least one of a large, hydrophilic head group; an unsaturated structure; and/or a branched structure; constitutes a viable advancement and alternative in the realm of antimicrobial formulations. The antimicrobial compositions of the present invention are adapted for direct application to human skin, without causing dryness or irritation. Moreover, the antimicrobial compositions of the present invention are designed for use with or without water, and provide immediate and residual effectiveness in either instance against a variety of viruses and bacteria, including rotavirus, rhinovirus, respiratory syncytial virus (RSV), coronavirus, Gram-positive and Gram-negative bacteria.

The specific, anionic surfactant of the present invention presents a particularly novel aspect of the present compositions. Those of skill in the art have generally relied upon the incorporation of longer chain (i.e. $C_{12}$ to $C_{16}$) anionic surfactants into antimicrobial compositions. Conventional surfactants, comparable to the acyl components found in the phospholipid matrix of the cell membrane of bacteria and virus, are thought to possess optimum antimicrobial activity with reduced skin tissue penetration. However, conventional anionic surfactants have been associated with low solubility under acidic conditions, poor compatibility with cationic antimicrobial agents, slow dissolution kinetics and limited residual antimicrobial performance.

Against the conventional wisdom in the art, the short chain anionic surfactants of the present invention comprise at least one of the following characteristics: a large, hydrophilic head group; an unsaturated structure; and/or a branched structure. Indeed, the surfactants of the present invention have traditionally been regarded as unsuitable for incorporation into an antimicrobial composition, based on the belief that such surfactants possess relatively low surface activity. Contrary to the traditional wisdom, it has been surprisingly discovered that the surfactants of the present invention deliver enhanced antimicrobial efficacy against rotavirus, rhinovirus, respiratory syncytial virus (RSV), coronavirus, Gram-negative bacteria and Gram-positive bacteria. More importantly, the large head group, unsaturated structure and/or branched structure of the present surfactants reduces or limits their tendency to penetrate skin tissue, while maximizing the immediate and residual effectiveness of the antimicrobial compositions in which they are incorporated. Further, the anionic surfactants of the present invention exhibit stability in an aqueous product at a low pH, are compatible with cationic antimicrobial agents and convey strong residual antimicrobial activity when the substrate on which they are applied is later inoculated with virus or bacteria.

Thus, in accordance with a first aspect of the present invention, antimicrobial compositions, comprising an organic acid or organic acid mixture, a specific, short-chain anionic surfactant mixture are disclosed. Against the conventional wisdom in the art, suitable anionic surfactants for use in the context of the present invention comprise a chain length of from about $C_4$ to $C_{12}$ and at least one of the following characteristics: a large, hydrophilic head group; an unsaturated structure; and/or a branched structure. In yet another aspect of the present invention, the antimicrobial compositions disclosed herein optionally further comprise a calcium ion scavenger and/or an anti-foam agent. The compositions of the present invention are adapted to provide immediate and residual kill of numerous bacteria and viruses, with or without the use of water and without causing dryness or irritation to skin.

In accordance with a second aspect of the present invention, products incorporating the antimicrobial compositions of the present invention are disclosed. Such products may take an assortment of shapes and forms depending on the precise application for which deployment of the product is desired and the needs and/or abilities of the formulator. In any instance, the products of the present invention are effective in eradicating numerous bacteria and viruses, both immediately and residually and are adapted to prevent dryness and/or irritation to mammalian skin tissue.

In accordance with a third aspect of the present invention, methods of using the antimicrobial compositions and products of the present invention are disclosed. The methods of the present invention are adapted to achieve immediate and/or residual kill of a variety of viruses and bacteria, without irritating the skin and with or without the use of water.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Antimicrobial Compositions

In accordance with a first aspect of the present invention, antimicrobial compositions, adapted for immediate and residual efficacy against a variety of bacteria and viruses, are provided. The compositions of the present invention comprise an organic acid or organic acid mixture; an anionic surfactant having a chain length of from about $C_4$ to about $C_{12}$ and at least one of the following characteristics: an unsaturated structure, a branched structure; and/or a hydrophilic head group having a total head group size (defined, infra) of between about 4 to about 15 Angstroms. In another aspect of the present invention, the antimicrobial compositions disclosed herein optionally further comprise a calcium ion scavenger and/or anti-foam agent. The compositions of the present invention are characterized by a pH of between about 2.0 to about 4.5, depending on the specific constituents of the present antimicrobial compositions and the application for which their use is intended.

Organic Acid

Indeed, in one aspect of the present invention, the antimicrobial compositions disclosed herein comprise an amount of an organic acid or organic acid mixture. Organic acids, for purposes of the present disclosure, are defined as proton-donating agents that remain at least partially undisassociated in a concentrated composition and remain so when the compositions are diluted during washing and rinsing. Without wishing to be bound by theory, the organic acids of the present invention serve to protonate the carboxylate functionalities on the phospholipid membrane of bacteria and virus and reduce the tendency of the membrane to electronically repel anionic surfactants, thereby facilitating proper interaction between the present, anionic surfactants and the membrane. Moreover, the organic acids disclosed herein facilitate the creation of a low pH buffer on the surface of a substrate, thereby prolonging the residual antimicrobial activity of the compositions and products in which they are incorporated.

Preferably, the present organic acids are added directly to the compositions of the present invention in acidic form or are formed by adding the conjugate base of the desired acid and an amount of a separate acid sufficient to form the undisassociated acid from the base. The antimicrobial compositions of the present invention comprise from about 0.2% to about 70%, preferably about 0.5% to about 40%, more preferably from about 1.0% to about 30%, based on the total weight of the antimicrobial composition, of an organic acid or organic acid mixture.

Suitable organic acids of the present invention include, but certainly are not limited to: pyroglutamic acid, adipic acid, gluconic acid, glyconolactone acid, glutamic acid, glycolic acid, glutaric acid, tartaric acid, ascorbic acid, benzoic acid, salicylic acid, citric acid, malic acid, succinic acid, lactic acid, carboxymethylcellulose and mixtures thereof. In another aspect of the present invention, suitable organic acids for incorporation into the present compositions are characterized by a pKa of greater than about 3.0. Without wishing to be bound by theory, the pKa selection limitation of the present organic acids serves the fundamental goal of ensuring that at least 50% of the organic acids incorporated into the present compositions remain undisassociated at the desired pH of from about 2.0 to about 4.5 (discussed, infra).

Optional Calcium Ion Scavenger

In another aspect of the present invention, the compositions disclosed herein comprise a calcium ion scavenger. Without wishing to be bound by theory, the calcium ion scavengers of the present invention, too, facilitate the disruption of the cell membrane of bacteria and viruses by the present, anionic surfactants via capture of the calcium ions of the phospholipid cell membrane. Without wishing to be bound by theory, said calcium ions are believed to exist within and around the cell membrane, thereby often preventing the penetration of conventional surfactants. The present, calcium ion scavengers are a particularly preferred ingredient of the present antimicrobial compositions when the targeted microbial is rotavirus. Suitable calcium ion scavengers of the present invention, include, but are not limited to: citric acid, malic acid, succinic acid, polyacrylic acid, copolymers of acrylic acid and maleic acid, oxydisuccinic acid, nitrilotriacetic acid, iminodisuccinic acid, tartrate disuccinic acid, tartrate monosuccinic acid, ethylenediaminetetraacetic acid, pyrophosphoric acid and mixtures thereof. In yet another aspect of the present invention, the calcium ion scavengers of the present invention are characterized by a pKa of lower than about 3.0. Moreover, in another aspect of the present invention, suitable calcium ion scavengers are characterized by a calcium ion binding constant (log P) of greater than about 3.0 at a pH of about 3.

Anionic Surfactant

The anionic surfactants of the present invention constitute a particularly novel and unobvious aspect of the present invention. Indeed, it has been surprisingly discovered that, contrary to the conventional wisdom in the art, anionic surfactants having a chain length of from about $C_4$ to about $C_{12}$ and at least one characteristic selected from: a large hydrophilic head group; an unsaturated structure; and/or a branched structure; provide enhanced performance benefits, while minimizing dryness and/or irritation to mammalian skin tissue. The short chain anionic surfactants of the present invention exhibit phase stability in formulation, compatibility with other antimicrobial agents and residual efficacy of the antimicrobial compositions in which they are incorporated. Without wishing to be bound by theory, it is believed that the interaction of short chain anionic surfactant with the phospholipid cell membrane of bacteria and virus, facilitated by the protonation of carboxylate functionalities at the surface of the membrane, disrupts the membrane and denatures cellular proteins, thereby providing rapid microbiocidal activity.

The antimicrobial compositions of the present invention comprise from about 0.1% to about 40%, preferably from about 0.2% to about 30%, more preferably from about 0.3% to about 20% of an anionic surfactant mixture. In another aspect of the present invention, the short-chain anionic surfactants disclosed herein are incorporated into the present, antimicrobial compositions at a level of greater than about 25%. In another aspect of the present invention, the anionic surfactants useful for incorporation into the present antimicrobial compositions comprise a relatively short carbon chain, preferably between about $C_4$ to about $C_{12}$, more preferably between about $C_6$ to about $C_{11}$, most preferably between about $C_6$ to about $C_{10}$. It should be noted, however, that, due to the fact that some surfactants suitable for incorporation into the present antimicrobial compositions are commercially available in mixed chain lengths, the average chain length of the resultant anionic surfactant mixture may differ from the above-described ranges.

To reiterate, those of skill in the art have generally avoided the incorporation of so-called "short-chain" anionic surfactants into antimicrobial compositions. This trend is believed to be due in part to the conventional wisdom in the art that short-chain anionic surfactants are characterized by decreased interfacial activity and decreased interaction with the phospholipid membrane of bacteria and virus, and thus, provide poor microbiocidal activity. Accordingly, those of skill in the art have generally relied upon the employment of anionic surfactants with chain lengths of from $C_{12}$ to $C_{16}$ in antimicrobial compositions. The chain lengths of such surfactants are comparable to those of the acyl components in the phospholipid membrane of bacteria and virus, and thus, are thought to provide optimum microbiocidal activity. Moreover, longer chain surfactants have conventionally been thought to be less capable of skin penetration, and thus, less likely to cause dryness and irritation to skin. Nevertheless, conventional, longer chain anionic surfactants often exhibit poor phase stability in an acidic product matrix, incompatibility with cationic antimicrobial agents and decreased residual antimicrobial activity. Conversely, the shorter chain anionic surfactants of the present invention exhibit surprisingly high immediate microbiocidal activity, phase stability in broad concentration ranges of acidic aqueous matrices and compatibility with cationic antimicrobial agents. Importantly, the anionic surfactants of the present invention prevent dryness or irritation to skin and demonstrate strong residual microbiocidal activity on a target substrate when the substrate is later inoculated with bacteria or virus.

In another aspect of the present invention, the short chain anionic surfactants disclosed herein possess an unsaturated structure and/or a branched, hydrophobic group with a total carbon content ranging from about $C_4$ to about $C_{12}$, preferably from about $C_6$ to about $C_{11}$ and more preferably from about $C_6$ to about $C_{10}$. In yet another aspect of the present invention, the short-chain anionic surfactants disclosed herein comprise a hydrophilic head group with a total head group size of less than about 15 Angstroms, preferably less than about 10 Angstroms, more preferably between about 4 to about 7 Angstroms. By "total head group size," it is meant the accumulated size of every substituent on the hydrophilic head group of the present anionic surfactants. That is to say, the present anionic surfactants may comprise more than one substituent on their subject hydrophilic head groups, for a combined, total hydrophilic head group size falling within the above-listed, ranges. Without wishing to be bound by theory, it is believed that the unsaturated structure and/or branched structure and/or large hydrophilic head group of the present, anionic surfactants increases their water solubility, increases their compatibility with cationic agents, increases steric hindrance to their disruption of the stratum conium layer of skin and maintains their substantivity to the phospholipid membrane of bacteria and viruses.

The "hydrophilic head group" is defined as the hydrophilic portion (which may contain both non-hydrocarbon and hydrocarbon units) of the anionic surfactant, measured from the first polar atom to the end of the hydrophilic segment that links to the hydrophobic body. For example, the hydrophilic head group of alkyl glyceryl sulfonate R—O—$CH_2CH(OH)$ $CH_2$—$SO_3Na$ is —O—$CH_2CH(OH)CH_2$—$SO_3Na$. The hydrophilic head group size is estimated from the Van der Waals radius of the atoms and the configuration of the surfactant molecule. Suitable hydrophilic head groups of the present invention with a size of less than about 10 Angstroms include, but are not limited to: glyceryl ether sulfonates and, for compositions having a pH of greater than 3.5, isethionates, sulfosuccinates, amidosulfonates and ethoxylated sulfonates.

In yet another aspect of the present invention, the head group of the anionic surfactant is characterized by substitution of one or more substituents. By "substituents" it is meant any hydrophilic segment that is bonded to the head group, defined hereinbefore, of the present anionic surfactants. Without wishing to be bound by theory, it is believed that such increased substitution on the head group of the present anionic surfactants further increases the size and hydrophilicity of the head group. Suitable hydrophilic head groups of the present invention with multiple substituents include, but are not limited to, alpha sulfo fatty acid, and if the pH of the present antimicrobial compositions is greater than 3.5, monoester of sulfosuccinic acid. To reiterate, the head group size of the present anionic surfactants is defined on the basis of Angstroms, as discussed supra. Thus, although the hydrophilic head group of the present anionic surfactants may comprise more than one substituent, the total hydrophilic head group size should not exceed the preferred size ranges, set forth hereinbefore, in Angstroms.

Accordingly, suitable anionic surfactants of the present invention, meeting all of the criteria discussed hereinbefore include, but certainly are not limited to: linear or branched alkyl glyceryl sulfonate, alkyl alpha sulfo fatty acid, alpha olefin sulfonate, branched alkyl sulfonate, branched alkyl benzene sulfonate, branched alkyl phosphonate and if the pH of the antimicrobial composition is greater than about 3.5, secondary alkyl sulfate, alkyl isethionate, monoester of alkyl sulfosuccinic acid, alkyl aminosulfonate, alkyl ethoxylated sulfonate, and combinations thereof. The aforementioned list is only intended to serve as a guide to the formulator of the present, antimicrobial compositions. Additional anionic surfactants having a chain length of from about $C_4$ to about $C_{12}$ and comprising at least one of the following characteristics are suitable for use herein: an unsaturated structure; a branched structure and/or a hydrophilic head group size as described hereinbefore. Selection of the appropriate anionic surfactant for use in the antimicrobial compositions of the present invention will depend upon the needs and/or abilities of the formulator. In another aspect of the present invention, other surfactants, many commercially available, are incorporated into the antimicrobial compositions of the present invention. Said surfactants, although depending on the precise form of the desired antimicrobial composition, include, but certainly are not limited to: paraffin sulfonate, hydrolyzed methyl ester sulfonate, alkyl sulfosuccinate, alkyl glyceryl sulfonate, alpha olefin sulfonate, alkyl isethionate, secondary alkyl sulfate, branched alkyl benzene sulfonate, alkyl sulfate and combinations thereof.

It should be noted and underscored that selection of the appropriate anionic surfactant for use in the context of the antimicrobial compositions of the present invention will depend upon several factors, including, but certainly not limited to: the nature of the substrate for which use of the antimicrobial compositions disclosed herein is desired and the needs and/or abilities of the formulator and/or practitioner of the present compositions. For instances in which the mildness of the present antimicrobial compositions on skin is not an issue, short chain anionic surfactants having a hydrophilic head group size of less than about than 4 Angstroms and/or a linear structure may be suitable for use in the context of the present invention. Indeed, for instances in which mildness of the present compositions on skin is not a fundamental concern, suitable anionic surfactants for use in the context of the present invention include, but certainly are not limited to: sulfonates and sulfates having a linear chain with a chain length of from about $C_4$ to about $C_{12}$, preferably having a chain length of from about $C_6$ to about $C_2$, more preferably having a chain length of from about $C_8$ to about $C_{12}$.

Anti-Foam Agent

In another aspect of the present invention, the antimicrobial compositions disclosed herein comprise an anti-foam or suds suppression agent. Incorporation of said agents is particularly desired for applications in which the present antimicrobial compositions comprise high sudsing, short chain anionic surfactants such as alkyl glyceryl sulfonate and/or a level of anionic surfactant of greater than about 1 weight percent. Incorporation of an anti-foam agent or suds suppression system is further advantageous in compositions for which low foaming is desired, particularly when such foaming has the affect of decreasing the conveyance of antimicrobial dosage. In one aspect of the present invention, the antimicrobial compositions disclosed herein comprise an anti-foam or suds suppression agent, present at a level of from about 0.0001% to about 15%, preferably from about 0.001% to about 10%, most preferably from about 0.005% to about 5% by weight of the antimicrobial composition. In another aspect of the present invention, the anti-foam agent is present in an amount of at least 1 ppm by weight of the total composition. Without wishing to be bound by theory, it is believed that incorporation of an anti-foam agent or suds suppression system serves the fundamental goal of controlling the suds profile of the present compositions during production and ensuring the delivery of an optimum dosage of the present antimicrobials during employment. Indeed, suitable suds suppressing systems for use herein may comprise essentially any known antifoam compound that exhibits stability at a pH of about 2.0 to about 4.5, including, but not limited to, those selected from the group consisting of: silicone antifoam compounds, silicone emulsions, 2-alkyl and alkanol antifoam compounds, mineral oil emulsions, hydrocarbon oil emulsions, polyalkylene emulsions and combinations thereof.

Silicone suds suppressor technologies and other anti-foam agents useful herein are extensively documented in "Defoaming, Theory and Industrial Applications", Ed., P. R. Garrett, Marcel Dekker, N.Y., 1973, ISBN 0-8247-8770-6, incorporated herein by reference. See especially the chapter "Surfactant Antifoams" (Blease et al). See also U.S. Pat. Nos. 3,933, 672 and 4,136,045, both incorporated herein by reference. Highly preferred silicone suds suppressors are the compounded types known for use in antimicrobial compositions, including, for example, polydimethylsiloxanes having trimethylsilyl or alternate endblocking units. Such compounds may be compounded with silica and/or with surface-active nonsilicon components, as illustrated by a suds suppressor comprising 12% silicone/silica, 18% stearyl alcohol and 70% starch. A suitable, commercial source of the silicone active compounds is Dow Corning Corp.

Optional Nonionic Agent

In accordance with another aspect of the present invention, the antimicrobial compositions disclosed herein further comprise a nonionic agent. In one aspect of the present invention, suitable nonionic agents for use in the present compositions are selected from the group consisting of: alkyl polyols, alkyl alcohols, phenols, chloro phenols, polyphenols and mixtures thereof. Without wishing to be bound by theory, it is believed that the optional nonionic agent of the present invention serves many roles, including, but certainly not limited to, increasing the antibacterial efficacy, in both immediate and residual kill, of the organic acid and short chain anionic surfactant system of the present invention. Some alkyl polyols, such as 1-(2-ethylhexyl)glycerol ether, have conventionally been thought to inhibit bacteria, and thus, have traditionally been employed as preservatives in commercial cosmetic products. Indeed, it has surprisingly been discovered that use of alkyl polyols and alkyl alcohols in the present compositions has the affect of increasing the immediate and residual activity of the present compositions. When present, the nonionic agents of the present invention are incorporated into the present antimicrobial compositions in an amount of from about 0.1% to about 10%, preferably from about 0.1% to about 5%, more preferably from about 0.1% to about 3%, by weight of the total, antimicrobial composition. In another aspect of the present invention, when the antimicrobial compositions of the present invention comprise a nonionic agent, said agent comprises a carbon chain length of from about $C_3$ to about $C_{12}$. Suitable nonionic agents for incorporation into the antimicrobial compositions of the present invention include, but certainly are not limited to: 1-(2-ethylhexyl) glycerol ether, octyl glycerol ether, 2-(2-ethylhexylxoxy) propanol, octyloxy propanol, 1-(2-ethylhexyloxy)ethanol, octyloxy ethanol, 1,2 hexylenediol, 1,2-cyclohexanedimethanol, isopropyl glycerol ether, 4-chloro-3-xylenol and combinations thereof. In another aspect of the present invention, the nonionic agent is branched, unsaturated or linear. In yet another aspect of the present invention, the nonionic agent is substituted with compounds selected from the group consisting of: alcohols, polyols, phenols, chloro phenols, polyphenols and combinations thereof.

Optional Adjunct Ingredients

In another aspect of the present invention, the compositions disclosed herein will comprise one or more adjunct ingredients. Said ingredients may be employed to increase the mildness of the desired composition, increase immediate and/or residual efficacy of the subject compositions, improve the wetting characteristics of the subject compositions upon application to a target substrate, operate as solvents for diluted compositions, and/or serve to modify the aesthetic characteristics of the composition. In one aspect of the present invention, the compositions disclosed herein comprise from about 0% to about 70%, preferably from about 0% to about 62%, more preferably from about 0% to about 10%, of an alcohol solvent. Suitable alcohol solvents of the present invention include, but are not limited to, ethanol, propanol, butanol, probpylene glycol, diethylene glycol, dipropylene glycol and mixtures thereof.

In another aspect of the present invention, the compositions disclosed herein comprise from about 0% to about 10%, preferably from about 0% to about 5%, more preferably from about 0% to about 1%, of a cationic antimicrobial agent. Depending on the region in which the formulator chooses to practice the present compositions, the inclusion of one or more cationic surfactants may be necessary for the procurement of regulatory approval. Suitable cationic antimicrobial agents for use in the compositions of the present invention, include, but certainly are not limited to, benzalkonium chloride, benzethonium chloride, triclocarban, tricolsan, chlorhexidine and mixtures thereof.

In yet another aspect of the present invention, the compositions disclosed herein comprise from about 0% to about 5%, preferably from about 0% to about 2%, of a heavy metal salt selected from the group consisting of: silver, zinc, copper and mixtures thereof. Incorporation of said heavy metal salt serves to increase the antimicrobial activity and the viscosity of the present, antimicrobial compositions. Moreover, the other ingredients of the present compositions have exhibited compatibility with the heavy metal salts disclosed herein. In another aspect of the present invention, the compositions disclosed herein comprise from about 0% to about 20%, preferably from about 0% to about 5%, of a skin emollient or moisturizer. Such ingredients serve the fundamental purpose of increasing the mildness (discussed infra) of the present antimicrobial compositions and are particularly desired when incorporating the present antimicrobial compositions into a skin care product (discussedinfra).

In yet another aspect of the present invention, one or more adjunct ingredients are incorporated into the antimicrobial compositions disclosed herein, to facilitate formulation of the desired composition. Those of skill in the art will readily appreciate that the inclusion of additional adjunct ingredients is often necessary to formulate certain ingredients included in the present compositions and in antimicrobial compositions generally. Indeed, it has been discovered, and documented via the present disclosure, that the formulation of certain perfumes and/or skin emollients in antimicrobial compositions requires the use of alkyl polyether-type emulsifiers. It has been learned that the use of said alkyl polyether-type emulsifiers is necessary to achieve physical stability of the resultant antimicrobial product when attempting to formulate certain perfumes and/or skin emollients. Although other types of emulsifiers are commercially available and often used in the context of formulation of antimicrobial-type compositions, the inventors of the subject matter disclosed herein have discovered that the use of emulsifiers other than those of the alkyl polyether-type, results in a chemically instable, yet efficacious, end product Thus, in yet another aspect of the present invention, the antimicrobial compositions disclosed herein comprise from about 0.05% to about 5%, preferably from about 0.1% to about 1%, more preferably from about 0.2% to about 0.5% of an alkyl polyether-type emulsifier. Non-limiting examples of alkyl polyether-type emulsifiers suitable for incorporation into the antimicrobial compositions disclosed herein include: isoceteth-20 (CAS No. 69364-63-2) and ceteth-20 (CAS No. 9004-95-9). In yet still another aspect of the present invention, use of the alkyl polyether-type emulsifiers disclosed herein are provided for use in the context of formulation of any antimicrobial composition comprising one or more otherwise physically instable adjunct ingredients, and not specifically limited to the antimicrobial compositions disclosed herein. In this respect, examples of said otherwise physically instable adjunct ingredients, include, but certainly are not limited to: perfumes, skin emollients, other nonionic agents and mixtures thereof.

In yet still another aspect of the present invention, other ingredients are included into the antimicrobial compositions to achieve physical stability for perfumes, skin emollients and other adjunct incorporated therein that otherwise exhibit physical instability absent the use of such adjuncts. Accordingly, the present invention further seeks to encompass the use of sulfonate anionic surfactant having a chain length of $C_{12}$ to $C_{18}$ are suitable for use in the context of the antimicrobial compositions disclosed herein, and are particularly preferred when the formulator of the present compositions seeks to incorporate certain adjuncts such as perfumes, skin emollients and combinations thereof. Thus, in accordance with this aspect of the present invention, the antimicrobial compositions disclosed herein comprise from about 0 to about 5%, preferably from about 0.1% to about 2%, more preferably from about 0.2% to about 1%. Suitable sulfonate anionic surfactants for use in the context of the present invention include, but certainly are not limited to: $C_{14\text{-}18}$ paraffin sulfonate and $C_{14\text{-}18}$ alkyl alpha olefin sulfonate. To reiterate, the incorporation of sulfonate anionic surfactants is particularly preferred in the context of the present invention when the formulator of the present compositions seeks to include perfumes, skin emollients and combinations thereof.

pH of Antimicrobial Compositions

It is fundamental to achieving the benefits of the present invention that the undisassociated acid from the organic acids disclosed hereinbefore remain on the skin in the protonated form. Thus, the pH of the antimicrobial compositions of the present invention must be adjusted to a sufficiently low level in order to either form or deposit substantially undisassociated acids onto the substrate for which treatment is desired. By "substantially undisassociated," it is meant that, upon application of the present compositions onto a target substrate, such as mammalian skin, about 30%, preferably 50%, more preferably 70%, of the organic acids incorporated in said compositions remain undisassociated following the elapse of about 30 minutes from application. The pH of the present compositions should be adjusted and preferably buffered to achieve the desired range. In another aspect of the present invention, the antimicrobial compositions disclosed herein are characterized by a pH of from about 2.0 to about 4.5, preferably from about 2.5 to about 4.0. Indeed, the pH of the antimicrobial compositions of the present invention will depend upon the precise ingredients incorporated into the subject compositions. Nevertheless, the pH of the present compositions is generally, and preferably, above about 2.0, as compositions characterized by a pH below 2.0 are typically required to be identified as toxic or hazardous materials.

Mildness of Antimicrobial Compositions

Topically applied products, including rinse-off cleansers and leave-on sanitizers, have conventionally possessed the tendency to irritate or dry mammalian skin. The compositions of the present invention, however, provide immediate and residual kill of bacteria and viruses, while possessing the fundamental characteristic of mildness. By "mildness" it is meant the degree to which a composition prevents dryness or irritation to skin. Factors that influence the mildness of a topically applied antimicrobial product include, but are not limited to, duration of exposure to the product, the frequency of use of the product and the degree to which the skin is occluded following exposure to the product.

Irritation is observed by several methods, including but not limited to, visual and instrumental assessment of the erythema for redness and of the skin for edema following application of an antimicrobial product. Irritation may be measured by determining the transepidermal water loss (TEWL) of skin before and after exposure to an antimicrobial product, using, for example, a TEWL meter. Indeed, products that cause irritation may eventually compromise the natural barrier function of mammalian skin—resulting in increased water loss' through the epidermis. Dryness is observed by several methods including, but not limited to, visual and instrumental assessment of the level and severity of dry skin flakes following exposure to an antimicrobial product. Dryness may be measured by instruments that examine the water content of the skin. One such instrument, a corneometer, measures the water content of skin via capacitance.

The present invention, despite its enormous cleaning and antimicrobial characteristics, is adapted to ensure increased mildness to mammalian skin upon application, particularly when compared to conventional cleansers such as bar or liquid soap and leave-on sanitizers. Indeed, the efficacy and mildness of the compositions of the present invention has been examined and illustrated under a variety of use conditions and methods. Namely, during a 10-day clinical forearm study, subjects applying the compositions of the present invention experienced significantly less skin irritation and dryness than subjects engaging in the same number of washes per day with soap and water and subjects applying conventional alcohol-based hand sanitizers. The results of the aforementioned study were measured using both visual and instrumental methods. The 10-day clinical forearm study is intended to mirror the hand washing and/or sanitizer use frequency typically recommended for proper hygiene. In another study, the leave-on application of the present compositions was applied 4 times daily, in addition to normal hand washing, and resulted in no measurable skin irritation or dryness.

Products Incorporating Antimicrobial Compositions

The present invention further relates to products that comprise the antimicrobial compositions of the present invention, as well as combinations of such products. Indeed, the combined and systematic use of products containing the antimicrobial compositions of the present invention serves to eradicate viruses (e.g. rhinovirus, rotavirus, respiratory syncytial virus (RSV), coronavirus) and bacteria (e.g. Gram-positive and Gram-negative) for a longer period of time and prevent their spread.

Personal Care Products

Thus, in accordance with a first aspect of the present invention, personal care products comprising the antimicrobial compositions of the present invention are disclosed. Suitable personal care products comprising the antimicrobial composition of the present invention, include, but are not limited to: hand soaps, hand sanitizers, body washes, mouth washes, toothpastes, shower gels, shampoos, body lotions, deodorants, nasal sprays, foot care, vaginal care and/or wash, pet care and combinations thereof. In yet another aspect of the present invention, the personal care products disclosed herein take the form of a wipe product, particularly suitable for wiping or drying the face or hands. In such instance, the antimicrobial compositions of the present invention are preferably embedded or impregnated into said wipe product. In yet still another aspect of the present invention, the personal care product disclosed herein takes the form of a tissue or towel, also suitable for wiping or drying the face or hands. In another aspect of the present invention, the personal care product takes the form of a feminine napkin and/or a diaper. In another aspect of the present invention, the personal care product takes the form of a first aid antiseptic for irritated, injured, or acne-affected skin and/or for pre or post surgical use.

Household Care Products

In another aspect of the present invention, the antimicrobial compositions of the present invention are incorporated into one or more household care products. Indeed, suitable household care products for purposes of the present invention include, but are not limited to: hard surface cleaners, deodorizers, fabric care compositions, fabric cleaning compositions, manual dish detergents, automatic dish detergents, floor care compositions, kitchen cleaners or disinfectants, bathroom cleaners or disinfectants and combinations thereof. In another aspect of the present invention, the household care product takes the form of a wipe or towel, suitable for household cleaning and/or care. In yet another aspect of the present invention, the household care products disclosed herein comprise certain adjunct ingredients. Said adjuncts include, but certainly are not limited to: detersive enzymes, builders, bleaching agents, bleach activators, transitional metal bleach catalysts, oxygen transfer agents and precursors, soil release agents, clay soil removal and/or anti-redeposition agents, polymeric dispersing agents, brightener, polymeric dye transfer inhibiting agents, chelating agents, anti-foam agents, alkoxylated polycarboxylates, fabric softeners, perfumes, carriers, hydrotropes, processing aids, dyes or pigments, solvents for liquid formulations, solid fillers, detersive surfactants and combinations thereof.

Skin Care Products

In another preferred aspect of the present invention, the antimicrobial compositions of the present invention are incorporated into a skin care product. In one aspect of the present invention, the skin care product incorporates a dermatologically acceptable carrier to facilitate safe transfer of the antimicrobial composition of the present invention to the desired area of the skin. In another aspect of the present invention, the skin care product of the present invention comprises certain adjunct ingredients. Said adjuncts include, but certainly are not limited to: antimicrobial and antifungal actives, surfactants, desquamation actives, anti-acne actives, anti-wrinkle actives, anti-atrophy actives, anti-oxidants, radical scavengers, chelators, flavonoids, anti-inflammatory agents, anti-cellulite agents, topical anesthetics, tanning actives, sunscreen actives, conditioning agents, thickening agents, detackifying agents, odor control agents, skin sensates, antiperspirants and mixtures thereof. Indeed, a complete description and examples of each of the aforementioned adjunct ingredients is set forth in U.S. Pat. No. 6,294,186, assigned to The Procter and Gamble Company, Cincinnati, Ohio and incorporated herein by reference.

Articles of Manufacture & Kits

Moreover, articles of manufacture comprising the antimicrobial compositions of the present invention and/or one or more of the aforementioned products, are intended for personal care, skin care and household care applications. The article of manufacture of the present invention encompasses one or more products as described hereinbefore that may be packaged in a container or dispenser with a set of instructions for the consumer. The article of manufacture of the present invention typically comprises (a) container or dispenser, (b) product and (c) set of instructions to apply said product to an appropriate substrate to achieve immediate and residual antimicrobial activity. Containers and/or dispensers suitable for the article of manufacture of the present invention include, but are not limited to: PET bottles and tubs, flow-wrap pouches, foaming dispensers, spray dispensers and combinations thereof. To reiterate, the article of manufacture of the present invention further comprises a set of instructions in association with the container. By "in association with," it is meant that the instructions are either directly printed on the container or dispenser itself or presented in a different fashion including, but not limited to: a brochure, print advertisement, electronic advertisement and/or verbal communication, so as to communicate the set of the instructions to a consumer of the article of manufacture.

The set of instructions typically comprise the instructions relating to the use of the product to apply the antimicrobial composition of the present invention onto a suitable substrate for which treatment is sought. The set of instructions may further comprise the instruction to allow the antimicrobial composition of the present invention to remain on the treated substrate, without rinsing or otherwise removing the antimicrobial composition from the treated substrate. Nevertheless, the precise instructions included with the article of manufacture of the present invention will depend on the precise ingredients of the subject antimicrobial composition and the product for which the inclusion of instructions is desired and the substrate onto which application of the product is intended. In another aspect of the present invention, the instructions included in the present articles of manufacture coincide with the methods set forth in the "Methods of Use" section of the present disclosure.

Methods of Use

The antimicrobial compositions and products of the present invention are suitable for a variety of uses. Indeed, suitable uses of the present compositions include, but certainly are not limited to, the eradication of viruses and/or bacteria; the provision of residual anti-viral efficacy; the provision of residual antibacterial efficacy; the prevention and/or treatment of a common cold or associated respiratory disease in a mammal; the prevention and/or treatment of a diarrhea disease in a mammal; the prevention and/or treatment of bacteria-related diseases in mammals resulting from contact with a bacteria-infected surface; the sanitization of hard surfaces; the improvement of the overall health of a mammal; the reduction of absenteeism; the prevention and/or treatment of dandruff and acne; and combinations thereof. It should be noted that, in the case of preventing or treating a common cold or respiratory disease, treatment with the compositions and products disclosed herein is effective when the cold or respiratory disease is caused by rhinovirus, coronavirus or RSV. It should be noted that, in the case of diarrhea, treatment with the present compositions and/or products is effective when the diarrhea is caused by rotavirus or bacteria.

Indeed, in one aspect of the present invention, a method of killing bacteria is provided. Said method comprises the steps of topically applying the composition and/or product of the present invention to an area in need of treatment and, optionally, removing said composition and/or product following application. In another aspect of the present invention, a method of inactivating viruses is disclosed. Said method, too, comprises the steps of topically applying the composition and/or product of the present invention to an area in need of treatment and, optionally, removing said composition and/or product following application. The method of inactivating viruses is useful in treating viruses selected from the group consisting of: rotavirus, rhinovirus and combinations thereof.

Indeed, in another aspect of the present invention, a method of providing residual antibacterial and antiviral efficacy is provided. Said method preferably comprises the steps of topically applying the composition and/or product of the present invention to an area in need of treatment and, optionally, removing said composition following application. In yet another aspect of the present invention, a method of preventing and/or treating a respiratory disease or diarrhea in a mammal where the sickness is caused by a rhinovirus, coronavirus, RSV or rotavirus, respectively, is envisioned. Said method comprises the steps of topically applying the composition and/or products of the present invention to an area of the mammal in need of treatment and, optionally, removing said composition and/or product following application. Moreover, the present invention seeks to encompass a method of preventing and/or treating bacteria-related diseases in a mammal that result from said mammal's contact with a bacteria-infected substrate. Said method comprises the steps of topically applying the composition and/or product of the present invention to an area of the mammal that is infected with said bacteria and, optionally, removing said composition and/or product following application.

To reiterate, each of the methods of the present invention comprise the step of topically applying a composition or product comprising same to an area or surface in need of treatment. Examples of areas and/or surfaces in need of treatment, against which the compositions of the present invention are effective, include, but are not limited to: one or more hands, a nose, a nasal canal or passage, an article of clothing, a hard surface, irritated, acne-affected, or injured skin, pre or post surgical areas and combinations thereof.

The exact amount of antimicrobial composition and/or nature of a product will depend upon the needs and abilities of the formulator and practitioner of the present methods. Nevertheless, when the antimicrobial compositions or products of the present invention are topically applied to keratinous tissue, e.g. adult hands, they are applied in doses of from about 0.1 mL to about 5 mL per use, more preferably 0.5 mL to about 4 mL, most preferably from about 1 mL to about 3 mL. Moreover, the compositions and products of the present invention are topically applied to surfaces in need of treatment from about 2 to about 6 times daily. Once applied, the compositions are rubbed on the treated surfaces for a period of time to ensure coverage, typically at least 5 seconds, preferably at least 10 seconds, more preferably at least 20 seconds and most preferably at least 30 seconds.

PREPARATIVE EXAMPLES

The antimicrobial compositions and products of the present invention were prepared in accordance with the present disclosure. Table 1 and 2, set forth as follows, summarizes the preparation of sixteen antimicrobial compositions in accordance with the present invention. Example 12 and 16 relate to the preparation of a concentrated version of the antimicrobial compositions of the present invention. The product solution of Examples 1 to 12 in Table 1 changed opacity from clear to hazy over time, due to the slow hydrolysis of hydrogenated castor oil. However, the antimicrobial efficacy of the solutions included therein remained unaffected. Contrarily, Examples 13 to 16 in Table 2 remained stable as clear aqueous solutions with consistent antimicrobial performance after prolonged storage under stressed conditions (e.g. one month at 45 degree C.). Moreover, Tables 3 to 6 summarize the efficacy of a few examples, the preparation of which is summarized in Tables 1 and 2. The following disclosure further includes a discussion of the testing methods and results of the compositions disclosed herein, as well as methods for preparing one or more products in accordance with the present invention.

TABLE 1

COMPOSITIONAL EXAMPLES

| Component | EX 1 | EX 2 | EX 3 | EX 4 | EX 5 | EX 6 | EX 7 | EX 8 | EX 9 | EX 10 | EX 11 | EX 12 (Conc) |
|---|---|---|---|---|---|---|---|---|---|---|---|---|
| Sodium Octyl Glyceryl Sulfonate | 0.5 | 0.5 | 0.5 | 0.5 | 0.5 | 0.5 | 0.5 | 0.5 | 0.5 | 0.5 | 0.5 | 15 |
| Sodium Salt Pyrrolidone Carboxylate | 0.5 | 0.5 | 0.5 | 0.5 | 0.5 | 0.5 | 0.5 | 0.5 | 0.5 | | 0.5 | |
| Gluconic Acid | | | | | | | | | | 1.5 | 1.5 | 15 |
| Hydrogenated Castor Oil | 0.1 | 0.1 | 0.1 | 0.1 | 0.1 | 0.1 | 0.1 | 0.1 | 0.1 | 0.1 | 0.1 | 1.0 |
| Perfume | 0.05-0.1 | 0.05-0.1 | 0.05-0.1 | 0.05-0.1 | 0.05-0.1 | 0.05-0.1 | 0.05-0.1 | 0.05-0.1 | 0.05-0.1 | 0.05-0.1 | 0.05-0.1 | 0.5-1.0 |
| Citric Acid anhydrous | 1.5 | 1.5 | 1.5 | 1.5 | 1.5 | 1.5 | 1.5 | 1.5 | | 0.5 | | 5 |
| Malic Acid | | | | | | | | | | | 1.5 | |
| Methyl Cellulose | | 1.0 | | | | | | | | | | 1.0 |
| 3[(2-Ethyhexyl)oxy]1,2 Propanediol | | | 0.5 | | | | | | | | | |
| Benzalkonium Chloride | | | | 0.1 | | | | | | | | |
| Propylene Glycol | | | | | 3 | | | | | | | |
| 2-Propanol | | | | | | | 8 | | | | | |
| Aloe Vera | | | | | | | | 0.1 | | | | |
| Menthol | | | | | | | | | 0.1 | | | |
| PH adjusted by 1N NaOH | 3.0 | 3.0 | 3.0 | 3.0 | 3.0 | 3.0 | 3.0 | 3.0 | 3.0 | 3.0 | 3.0 | 3.0 |

TABLE 2

COMPOSITIONS EXAMPLES

| Component | EX 13 | EX 14 | EX 15 | EX 16 (Conc) |
|---|---|---|---|---|
| Sodium Octyl Glyceryl Sulfonate | 0.5 | 0.5 | 0.5 | 10 |
| Gluconic Acid | 2.0 | 2.0 | 2.0 | 20 |

TABLE 2-continued

COMPOSITIONS EXAMPLES

| Component | EX 13 | EX 14 | EX 15 | EX 16 (Conc) |
|---|---|---|---|---|
| Isoceteth-20 | | 0.35 | 0.35 | 2-5 |
| Propylene Glycol | | 0.1-0.3 | 0.25 | 2-5 |
| Perfume | | 0.075-0.125 | 0.15 | 1-2 |
| Methyl Cellulose | | | 1.0 | |
| Polyacrylic Acid (MW 3000-6000) | | | 0.25 | |
| Aloe Vera | | 0.1 | 0.2 | 2 |
| Menthol | | 0.05 | 0.15 | |
| Ethanol | | | 10 | |
| PH adjusted by 1 N NaOH | 3.0 | 3.0 | 3.0 | 3.0 |

TABLE 3

EFFICACY OF COMPOSITIONS

| Liquid Composition | Challenge Organism | Log reduction Time Kill (1 min): Suspension Test |
|---|---|---|
| EX 7 | E. coli ATCC 11229 | >4 |
| EX 7 | Corynebacterium striatum ATCC 6940 | >4 |
| EX 7 | Corynebacterium mucifaciens axillary isolate 29 | >3 |
| EX 7 | Staphylococcus epidermidis ATCC 35984 | 3 |
| EX 7 | Staphylococcus epidermidis axillary isolate 9 | >4 |

TABLE 4

EFFICACY OF COMPOSITIONS

| Liquid Composition | E. coli Log reduction Time Kill (1 min): solution & wipe | E. coli Log Reduction Immediate: Vitro skin | E. coli Log Reduction Residual: Vitro skin | Rotavirus Log Reduction Immediate: Vitro skin | Rotavirus Log Reduction Residual: Bio skin |
|---|---|---|---|---|---|
| EX 1 | 5 | 4 | 4 | 3 | |
| EX 3 | 5 | 5 | 5 | 3 | 3 |
| EX 4 | | 3 | 3 | | |
| EX 7 | | 4 | 4 | | |
| EX 8 | | 4 | 5 | | |
| EX 9 | | 4 | 4 | | |
| EX 10 | | 3 | 4 | | |
| EX 11 | 5 | 3 | 4 | 2 | |

TABLE 5

EFFICACY OF COMPOSITIONS

| CHALLENGE ORGANISM | EX 13 | EX 14 |
|---|---|---|
| E. coli 11229: | | |
| Log Reduction Immediate; Bio skin | 5 | 5 |
| Log Reduction Residual; Bio skin | 5 | 5 |
| Rotavirus Strain WA from University of Ottawa, Ontrio, Canada: | | |
| Log Reduction Immediate; Bio skin | 4 | 4 |
| Log Reduction Residual; Bio skin | 3 | 5 |

TABLE 5-continued

EFFICACY OF COMPOSITIONS

| CHALLENGE ORGANISM | EX 13 | EX 14 |
|---|---|---|
| Corona Virus ATCC 229 E: | | |
| Log Reduction Immediate; Bio skin | | 4 |
| Log Reduction Residual; Bio skin | | 4 |
| Rhinovirus ATCC 16: | | |
| Log Reduction Immediate; Bio skin | 4 | 4 |
| Log Reduction Residual; Bio skin | | 3 |
| RSV ATCC VR-26: | | |
| Log Reduction Immediate Bio skin | | 4 |

TABLE 6

EFFICACY OF WIPE PRODUCTS

| Wipe Product | E. coli Log reduction Time Kill (5 min): wipe substrate |
|---|---|
| EX 1 | 3 |
| EX 9 | 4 |

Compositional Testing

Antibacterial Efficacy Assay in Vitro Skin #1013 (IMS)/Bio Skin Black #10

Method: Assay in Vitro Skin/Bio Skin

Immediate Efficacy:

10 μL of test bacteria suspension was spread on mammalian skin and allowed to air dry for one minute, then 20 μL of the active solution was spread evenly over the treated skin and the preparation was allowed to rest uncovered for five minutes. The skin substrate was placed into a test tube containing 10 mL of extraction solution (Phosphate buffer with Triton X-100, Lecithin and Tween) and vortex for 30 seconds. A 50 μL aliquot was dispensed (via Spiral Biotech Autoplater) onto Trypticase Soy Agar+1.5% Tween 80 plates and viability was determined after 18 hours of incubation at 37° C. (CUF/ml).

Residual Efficacy:

20 μL of the active solution was spread evenly over mammalian skin and allowed to dry for 15 min. 10 μL of test bacteria suspension was spread evenly over the treated skin and the preparation was allowed to rest covered for five minutes. The skin substrate was placed into a test tube containing 10 mL of extraction solution (Phosphate buffer with Triton X-100, Lecithin and Tween) and vortex for 30 seconds. A 50 μL aliquot was dispensed via Spiral Biotech Autoplater onto Trypticase Soy Agar+1.5% Tween 80 plates and viability was determined after 18 hours of incubation at 37° C. (CUF/ml).

Method: Solution Assay—Bacterial Time Kill:

A 50 μL of test bacteria suspension (TSB) culture with a density of 1.0 E+09 CFUs/ml was mixed with 5 ml of the active solution. After one minute time, the inoculated solution was mixed with DE neutralizing broth (ratio 1:10). A 50-μL aliquot was dispensed via Spiral Biotech Autoplater onto a Trypticase Soy Agar plate. Viability was determined after 18 hours of incubation at 37° C. (CUF/ml).

Method: Viral Efficacy Assay in Vitro Skin #1013 (IMS)/Bio Skin Black #10 Immediate Efficacy:

10 μL of test virus suspension was spread on the skin substrate and allowed to air dry at room temperature then 25 μL of the active solution was spread evenly over the treated skin and the preparation was allowed to rest for five minutes. Following the exposure period, a sterile 1.5 ml cryovial containing 1.0 ml of elution medium was inverted over the sink substrate surface and extraction was performed. The solution was mixed and serial 10 fold dilution was performed. The dilutions were assayed for the presence of virus in a host system. The virus titer of the stock was determined by the median cell culture infective dose (TCID 50). Cytotoxicity to the host system (active solution) at tested concentrations was also determined. The virus-product mixture was assayed in numerous units of the host system. Median values of log 10 virus inactivation were calculated.

Residual Efficacy:

25 µL of the active solution was spread evenly over the skin and allowed to dry for 15 min. 10 µL of the test virus suspension was spread evenly over the treated skin and the preparation remained in contact for five minutes. Following the exposure period, a sterile 1.5 ml cryovial containing 1.0 ml of elution medium was inverted over the sink substrate surface and extraction was performed. The solution was mixed and serial 10 fold dilution was performed. The dilutions were assayed for the presence of virus in a host system. The virus titer of the stock was determined by the median cell culture infective dose (TCID 50). Cytotoxicity to the host system (active solution) at tested concentrations was also determined. The virus-product mixture was assayed in numerous units of the host system. Median values of log 10 virus inactivation were calculated.

Method: Microbial Susceptibly Test (MST) for Wet Wipes—Time Kill:

A test wipe was inoculated with 1.0 ml of virus suspension to cover one quarter of the folded wipe. 5 minutes after inoculation the treated wipe was placed into a sterile bag containing 100 ml of DE neutralizer medium, the bag was sealed and placed in the Stomacher for 2 minutes. After blending, a 50 µL aliquot was dispensed (via Spiral Biotech Autoplater) onto Trypticase Soy Agar+1.5% Tween 80 plates and viability was determined after 18 hours of incubation at 37° C. (CUF/ml).

Liquid Composition Preparation for Use in Products

Blend the liquefied Isoceteth 20 (Example 14-16), Hydrogenated Castor Oil (Example 1-12), Perfume, Menthol (Example 8, 14 and 15), Propylene Glycol (Example 5, 14, 15 and 16) and (2-Ethyhexyl) Glycerol ether (Example 3). Emulsify the pre-mixed blend to a pre-dissolved Sodium Glyceryl sulfonate solution. Add and dissolve Sodium Pyrrolidone Carboxylate (Example 1-9 and 11), Citric Acid (Example 1-10, 10 and 12), Gluconic Acid (Examples 9, 10, 12-16) and Malic Acid (Example 11). Add to mixture, Isopropanol (Example 6), Ethanol (Example 15), Aloe Vera (Example 7 and 14-16). Adjust pH to 3.0 by 1N Sodium Hydroxide solution or 1N Phosphoric Acid. Slowly add Benzalkonium chloride solution (Example 4). Add Methyl Cellulose (5% aqueous solution) during mixing (Example 2 and 15). Adjust pH to 3.0 by 1N Sodium Hydroxide solution or 1N Phosphoric Acid. Add remaining water to make a target product weight. Check final pH.

Products Preparation

Example 13

Antimicrobial Hand Sanitizer

To deliver the benefits of the present invention in a hand sanitizer form, the liquid composition produced in accordance with the previous section may be packaged in a typical PET bottle with a flip-top cap. Liquid is dispensed to the hands in an amount to ensure complete wetting. Employing this method delivers immediate microbial kill and, upon drying, provides prolonged, residual activity.

Example 14

Antimicrobial Wipe

The lotion produced in accordance with the previous section may be used to produce a wet wipe product for topical cleaning and/or sanitizing of skin and/or hard surfaces. Such a product is made by saturating a paper or cloth substrate with the liquid composition prepared in accordance with the previous section. The level of saturation depends upon the substrate in which incorporation of the antimicrobial composition is desired. A 5"×8" hand wipe towelette made from 40-60 grams per square meter spun-lace non-woven material may be saturated with about 1-3 grams of liquid composition. The liquid may be applied to the substrate via spraying and/or soaking prior to final packaging. The wipe may be wrapped in single use pouches made from foil or plastic or packed in groups of 10, 40, or more in multiple use tubs.

To deliver the benefits of the present invention in this form, the wipe is removed from its package and is rubbed onto the target surface, in a manner that ensures complete wetting of the surface. The wetting practice removes visible dirt and eradicates bacteria and viruses. Upon drying, the surface experiences residual antimicrobial activity for several hours.

Example 15

Antimicrobial Drying Towel

The lotion produced in accordance with the previous section may be used to produce a dry towel product for topical cleaning and/or sanitizing of skin or hard surfaces. Such a product is made by saturating a paper or cloth substrate with the liquid prepared in accordance with the preceding section. The substrate is then dried to remove all water. The level of saturation depends upon the substrate in which incorporation of the antimicrobial composition is desired. A 5"×8" towel made from 40-60 grams per square meter spun-lace non-woven material may be saturated with about 1-3 grams of liquid. The liquid may be applied to the substrate via spraying and/or soaking prior to final packaging. The liquid may also be applied in concentrate form using printing techniques employed in the color design of commercial, paper towels. The towel may then be rolled or inserted into boxes.

To deliver the benefits of the present invention in this form, the towel is applied to any wet skin or hard surface to dry it. The water activates the antimicrobial properties of the composition within the towel, which is then imparted onto the surface. Employing this method, the towel dries the target surface, removes visible dirt, delivers antimicrobial kill and provides prolonged, residual activity.

Example 16

Anti-Inflammatory Efficacy of RID Compositions

Indeed, the antimicrobial compositions, methods and products of the present invention have demonstrated surprising anti-inflammatory benefits in the topical treatment of inflammation or dermatitis. In vitro studies of the present invention and its key components have been conducted to assess the efficacy of the claimed compositions in inhibiting the cycloxygenase (COX) 1 and 2 enzymes. Said enzymes are adapted to convert arachidonic acid in cell membranes to prostaglandin, a messenger agent that conveys a signal to the cells to increase and enhance their inflammatory response. The results of the aforementioned in vitro study demonstrate that the present invention can significantly reduce the activity of both COX 1 and 2 enzymes. This is particularly important when considered in light of the fact that the key components of the present invention, namely, the short chain anionic surfactant with a large head group or branched structure, the organic acid, and the optional calcium ion-scavenging agent, demonstrate only limited efficacy upon employment individually. The results of this in vitro study have been documented in the below-listed chart.

| Treatment Sample | % of Initial Enzyme Activity | |
|---|---|---|
| (at pH 3.0) | COX-1 | COX-2 |
| A. 0.5% Octyl Glyceryl Sulfonate | 55 | 95 |
| B. 0.5% Pyroglutamic Acid | 100 | 92 |
| C. 1.5% Citric Acid | 94 | 100 |
| D. A + B + C | 43 | 53 |

All documents cite are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antimicrobial composition capable of inactivating viruses and bacteria consisting of:
   a. from about 0.2% to about 70% of an organic acid, which is selected from the group consisting of: pyroglutamic acid, adipic acid, gluconic acid, gluconolactone acid, glutamic acid, glutaric acid, glycolic acid, tartaric acid, ascorbic acid, benzoic acid, salicylic acid, citric acid, malic acid, succinic acid, lactic acid and combinations thereof; and
   b. from about 0.1% to about 40% of an anionic surfactant mixture having a characteristic selected from the group consisting of:
      i. a linear alkyl chain having a chain length of from about $C_4$ to about $C_{12}$ and a total hydrophilic head group size of at least about 4 Angstroms;
      ii. an unsaturated alkyl chain having a chain length of from about $C_4$ to about $C_{12}$;
      iii. a branched alkyl chain having a chain length of from about $C_4$ to about $C_{12}$; and
      iv. combinations thereof;
   c. a calcium ion scavenger, which is citric acid, malic acid, succinic acid, or polyacrylic acid;
   wherein said composition is characterized by a pH of from about 2.0 to about 4.5.

2. The composition of claim 1, wherein said anionic surfactant is selected from the group consisting of: alkyl glyceryl sulfonate, branched alkyl glyceryl sulfonate, alpha sulfo fatty acid, alpha olefin sulfonate, branched alkyl sulfonate, branched alkyl benzene sulfonate, secondary alkyl sulfate, mono ester of alkyl sulfosuccinic acid, alkyl isethionate, alkyl amidosulfonate, branched alkyl phosphonate, branched alkyl phosphate and combinations thereof.

3. The composition of claim 1, further wherein said anionic surfactant is substituted with a substituent selected from the group consisting of: sulfonate, sulfate, phosphonate and combinations thereof.

4. The composition of claim 1 wherein said organic acid is pyroglutamic acid.

5. The composition of claim 1 wherein said organic acid is characterized by a pKa of greater than about 3.0.

6. The composition of claim 1 wherein said calcium ion scavenger is citric acid.

7. The composition of claim 1 wherein said calcium ion scavenger is characterized by a pKa of lower than about 3.0.

8. The composition of claim 1 wherein said calcium ion scavenger is characterized by a calcium ion binding constant log P of greater than about 3.0 at a pH 3.

9. An antimicrobial product comprising the antimicrobial composition of claim 1.

10. The antimicrobial product according to claim 9, wherein said product is a personal care product.

11. The personal care product according to claim 10, wherein said personal care product is selected from the group consisting of: hand soaps, hand sanitizers, body washes, shower gels, shampoos, body lotions, feminine care products, foot care products, deodorants, pet care products and combinations thereof.

12. The antimicrobial product according to claim 9, wherein said product is a household care product.

13. The household care product of claim 12, wherein said product is selected from the group consisting of hard surface cleaners, deodorizers, fabric care compositions, fabric cleaning compositions, manual dish detergents, automatic dish detergents, floor waxes, kitchen cleaners, bathroom cleaners and combinations thereof.

14. The antimicrobial product according to claim 9, wherein said product is selected from the group consisting of: a wipe product suitable for personal care use and household cleaning; a toilet tissue; a towel for hand drying, household drying and household cleaning; a facial tissue; a skin care composition; a first aid or surgical antiseptic; a diaper; a feminine napkin; and combinations thereof.

15. The skin care composition according to claim 14, further comprising a dermatologically acceptable carrier for said antimicrobial composition.

16. A method of killing bacteria, said method comprising the steps of topically applying the composition of claim 1 to an area in need of treatment and, optionally, removing said composition following its application.

17. A method of inactivating viruses, said method comprising the steps of topically applying the composition of claim 1 to an area in need of treatment and, optionally, removing said composition following its application.

18. A method of providing residual antibacterial efficacy, said method comprising the steps of topically applying the composition of claim 1 to an area in need of treatment and, optionally, removing said composition following its application.

19. A method of preventing and/or treating a common cold, respiratory disease and diarrhea in a mammal where said diseases are caused by rhinovirus, rotavirus, coronavirus, respiratory syncytial virus and combinations thereof, said method comprising the steps of topically applying the composition of claim 1 to an area of the mammal in need of treatment and, optionally, removing said composition following its applications.

20. A method of preventing and/or treating bacteria-related diseases in a mammal that result from said mammal's contact with a bacteria-infected substrate, said method comprising the steps of topically applying the composition of claim 1 to an ear of the mammal which is infected with said bacteria and, optionally, removing said composition following its application.

21. A method of reducing inflammation, said method comprising the steps of topically applying the composition of claim 1 to an area in need of treatment, and optionally, removing said composition following its application.

22. The method according to claim 21 wherein said inflammation is caused by a source selected from the group consisting of:
    plants, diaper rash, insect bites, allergic inflammatory reactions and combinations thereof.

23. A method of preventing inflammation, said method comprising the steps of topically applying the composition of claim 1 to an area for which the prevention of inflammation is desired, and optionally, removing said composition following its application.

* * * * *